United States Patent [19]

Suzuki et al.

[11] Patent Number: 5,336,769
[45] Date of Patent: Aug. 9, 1994

[54] XANTHINE DERIVATIVES

[75] Inventors: Fumio Suzuki, Mishima; Junichi Shimada; Akio Ishii, both of Shizuoka; Shizuo Shiozaki, Fuji, all of Japan

[73] Assignee: Kyowa Hakko Kogyo Co., Ltd., Tokyo, Japan

[21] Appl. No.: 18,209

[22] Filed: Feb. 16, 1993

[30] Foreign Application Priority Data

Feb. 17, 1992 [JP] Japan .................................. 4-029662

[51] Int. Cl.$^5$ .............................. C07D 473/06
[52] U.S. Cl. .............................. 544/273; 544/272
[58] Field of Search .................. 544/270, 272, 273; 514/263

[56] References Cited

U.S. PATENT DOCUMENTS

| | | | |
|---|---|---|---|
| 4,061,753 | 12/1977 | Bodor et al. | 544/267 |
| 4,849,423 | 7/1989 | Ott | 544/272 |
| 4,879,296 | 11/1989 | Daluge et al. | 549/272 |
| 5,068,236 | 11/1991 | Suzuki et al. | 544/273 |

FOREIGN PATENT DOCUMENTS

| | | |
|---|---|---|
| 0203721 | 12/1986 | European Pat. Off. . |
| 0374808 | 6/1990 | European Pat. Off. . |
| 0415456 | 3/1991 | European Pat. Off. . |
| 0501379 | 9/1992 | European Pat. Off. . |
| WO8601724 | 3/1986 | PCT Int'l Appl. . |
| WO9200297 | 1/1992 | PCT Int'l Appl. . |

OTHER PUBLICATIONS

Patel et al., Mol. Pharmacol., vol. 33 (1988) pp. 585:91.
Merlos et al., Eur. J. Med. Chem. vol. 25 (1990) pp. 653:58.
Linden et al., J. Med. Chem. vol. 31 (1988) pp. 745:51.
Goldner et al., Chemical Abstracts 63 (1965).

*Primary Examiner*—Mukund J. Shah
*Assistant Examiner*—Pavanaram K. Sripada
*Attorney, Agent, or Firm*—Fitzpatrick, Cella, Harper & Scinto

[57] ABSTRACT

A xanthine derivative of the formula (I):

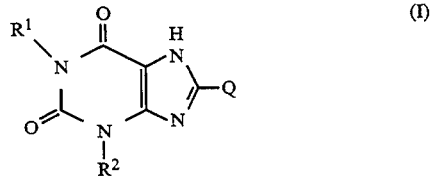

wherein $R^1$ represents substituted or unsubstituted lower alkyl, lower alkenyl, lower alkynyl, substituted or unsubstituted alicyclic alkyl, substituted or unsubstituted phenyl, or substituted or unsubstituted benzyl;

$R^2$ represents —$(CH_2)_m$—X, wherein m is 2 or 3, and X is

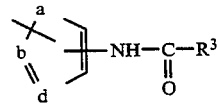

wherein a is NH, O or S, b and d are the same or different and are CH or N, and $R^3$ is lower alkyl, substituted or unsubstituted alicyclic alkyl, or substituted or unsubstituted phenyl, or

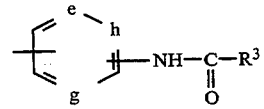

wherein e, g and h are the same or different and are CH or N, and $R^3$ is the same as defined above;

Q represents substituted or unsubstituted alicyclic alkyl,

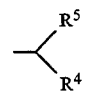

(Abstract continued on next page.)

wherein $R^4$ and $R^5$ are the same or different and are substituted or unsubstituted alicyclic alkyl,

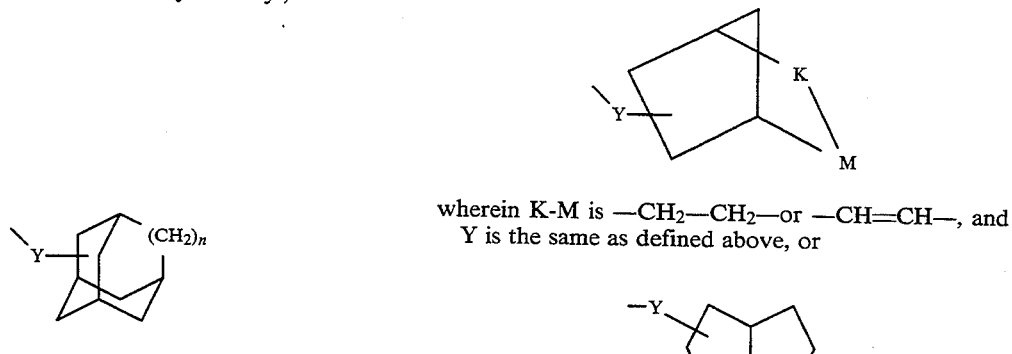

wherein K-M is —$CH_2$—$CH_2$—or —CH=CH—, and Y is the same as defined above, or wherein Y is single bond or alkylene; and n is 0 or 1, wherein Y is the same as defined above; or a pharmacologically acceptable salt thereof is disclosed.

This derivative has anti-dementia activity.

5 Claims, No Drawings

XANTHINE DERIVATIVES

BACKGROUND OF THE INVENTION

The present invention relates to xanthine derivatives having anti-dementia activity and being useful as an anti-dementia drug.

Xanthine derivatives have been hitherto known in the prior art. For example, Mol. Pharmacol., 33, 585 (1988) discloses a compound of the formula (A) having adenosine $A_1$ receptor antagonistic activity.

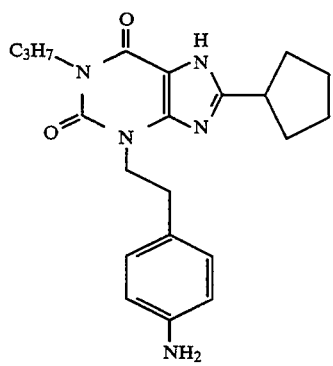

J. Med. Chem., 31, 745 (1988) discloses a compound of the formula (B) having adenosine $A_1$ receptor antagonistic activity.

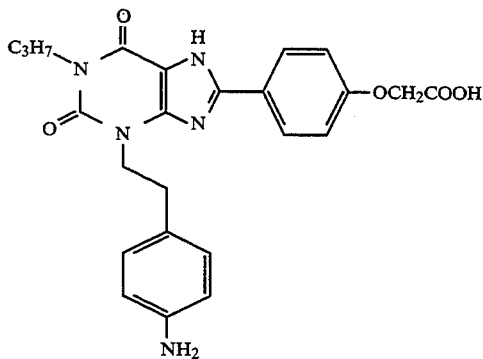

Eur. J. Med. Chem., 25, 653 (1990) discloses xanthine derivatives of the general formula (C):

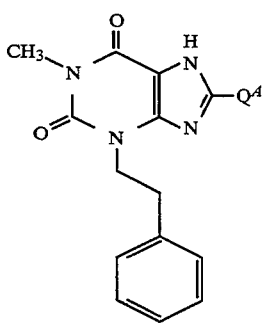

(wherein $Q^A$ represents alkyl) which exhibit bronchodilator activity.

Canadian Patent No. 724173 discloses xanthine derivatives of the general formula (D):

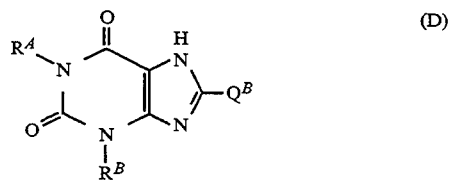

(wherein $R^A$ and $R^B$ represent alkyl or aralkyl, and $Q^B$ represents cycloalkyl) which exhibit diuretic activity.

Further, WO 86/01724 discloses an insecticide containing xanthine derivatives of the general formula (E):

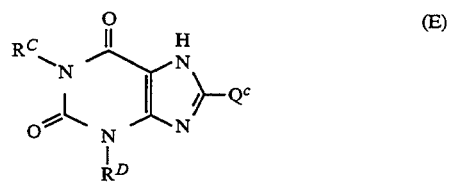

wherein $R^C$, $R^D$ and $Q^C$ are substituted or unsubstituted aliphatic or alicyclic hydrocarbon having 1 to 8 carbon atoms (substituents are selected from halogen, alkyl and hydroxy), substituted or unsubstituted aromatic hydrocarbon (substituents are selected from halogen, alkyl and hydroxy), or phenethyl.

EP 203721A (Japanese Published Unexamined Patent Application No. 42986/87) discloses xanthine derivatives of the general formula (F):

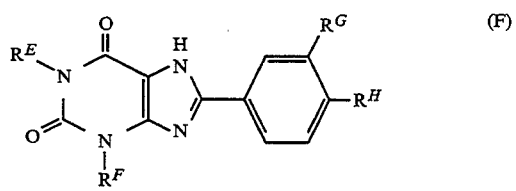

wherein $R^e$ and $R^F$ represent alkyl or amino-substituted aralkyl, and either $R^G$ or $R^H$ is hydrogen and the other is —Y—Z (wherein Y is alkenylene and Z is carboxyl). The xanthine derivatives have adenosine receptor antagonistic activity.

U.S. Pat. No. 5068236 (Japanese Publishes Unexamined Patent Application No. 173888/91) discloses xanthine derivatives of the formula (G):

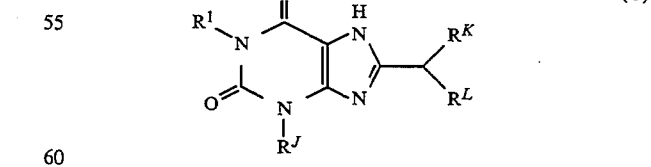

wherein $R^I$ and $R^J$ are lower alkyl; and $R^K$ and $R^L$ are substituted or unsubstituted alicyclic alkyl, The xanthine derivatives have exhibited diuretic activity, renal protecting activity and vasodilator activity.

EP 415456A (Japanese Publishes Unexamined Patent Application No. 173889/91) discloses xanthine derivatives of the formula (H):

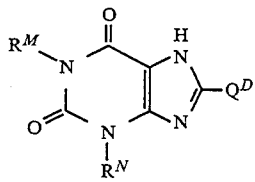

(H)

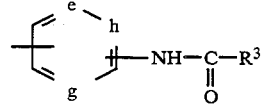

where $R^M$ and $R^N$ are lower alkyl; and $Q^D$ represents

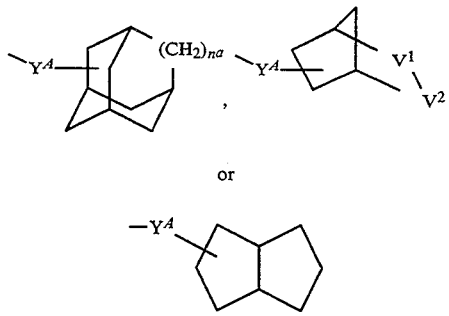

or

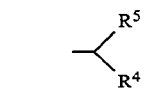

(wherein $V^1$-$V^2$ is —CH$_2$—CH$_2$— or —CH=CH—; $Y^A$ is a single bond or alkylene; and $n^a$ is 0 or 1). The xanthine derivatives have exhibited diuretic activity, renal protecting activity and bronchodilator activity.

SUMMARY OF THE INVENTION

The object of the invention is to provide novel xanthine derivatives having excellent anti-dementia activity.

This object as well as other objects and advantages of the present invention will become apparent to those skilled in the art from the following description.

The present invention provides a xanthine derivative of the formula (I) [hereinafter merely referred to as Compound (I)]

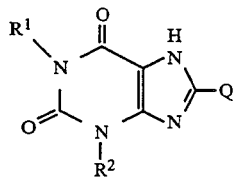

(I)

wherein $R^1$ represents substituted or unsubstituted lower alkyl, lower alkenyl, lower alkynyl, substituted or unsubstituted alicyclic alkyl, substituted or unsubstituted phenyl, or substituted or unsubstituted benzyl;

$R^2$ represents —(CH$_2$)$_m$—X, wherein m is 2 or 3, and X is

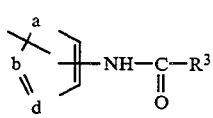

wherein a is NH, O or S, b and d are the same or different and are CH or N, and $R^3$ is lower alkyl, substituted or unsubstituted alicyclic alkyl, or substituted or unsubstituted phenyl, or wherein e, g and h are the same or different and are CH or N, and $R^3$ is the same as defined above;

Q represents substituted or unsubstituted alicyclic alkyl;

wherein $R^4$ and $R^5$ are the same or different and are substituted or unsubstituted alicyclic alkyl,

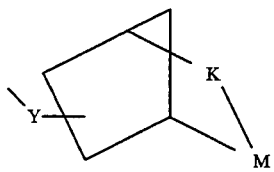

wherein Y is single bond or alkylene, and n is 0 or 1,

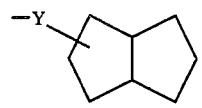

wherein K-M is —CH$_2$—CH$_2$— or —CH=CH—, and Y is the same as defined above or wherein Y is the same as defined above; and a pharmacologically acceptable salt thereof.

DETAILED DESCRIPTION OF THE INVENTION

In the definitions of the groups in the formula (I), examples of the alkyl moiety in the substituted or unsubstituted lower alkyl include straight or branched chain alkyl having 1 to 6 carbon atoms such as methyl, ethyl, propyl, isopropyl, butyl, isobutyl, sec-butyl, tert-butyl, pentyl, neopentyl and hexyl. Substituents of the lower alkyl are alicyclic alkyl having 3 to 8 carbon atoms, for example, cyclopropyl, cyclobutyl, cyclopentyl, cyclohexyl and cyclooctyl.

The lower alkenyl includes straight or branched chain alkenyl having 2 to 4 carbon atoms such as vinyl, allyl, propenyl, isopropenyl, butenyl and isobutenyl. The lower alkynyl includes straight or branched chain alkynyl having 2 to 4 carbon atoms such as propargyl and 3-butynyl.

Examples of the alicyclic alkyl moiety in the substituted or unsubstituted alicyclic alkyl include cycloalkyl having 3 to 8 carbon atoms such as cyclopropyl, cyclobutyl, cyclopentyl, cyclohexyl and cyclooctyl. The alicyclic alkyl, phenyl, allcyclic alkyl and benzyl may have 1 to 3 substituents and they are the same or different and are, for example, lower alkyl, hydroxy, lower alkoxy, halogen, nitro and amino. The alkyl moieties of the lower alkyl and the lower alkoxy are the same as those described above. The halogen includes fluorine, chlorine, bromine and iodine.

Examples of the alkylene represented by Y include straight or branched chain alkylene having 1 to 4 carbon atoms such as methylene, ethylene, trimethylene, tetramethylene, methylmethylene, propylene and ethylethylene.

The pharmacologically acceptable salt of Compound (I) includes pharmacologically acceptable acid addition salts, metal salts, ammonium salts, organic amine addition salts and amino acid addition salts.

As the pharmacologically acceptable acid addition salt, there are salts formed with inorganic acids such as hydrochloride, sulfate and phosphate, and salts formed with organic acids such as acetate, maleate, fumarate, tartrate and citrate. As the metal salt, there are alkali metal salts such as sodium salt and potassium salt, alkaline earth metal salts such as magnesium salt and calcium salt, aluminum salt and zinc salt. As the ammonium salt, there are ammonium salt, tetramethylammonium salt, and the like. As the organic amine addition salt, there are morpholine addition salt, piperidine addition salt, and the like. As the amino acid addition salt, there are lysine addition salt, glycine addition salt, phenylalanine addition salt, and the like.

Compound (I) can be produced according to the following reaction scheme:

wherein m is the same as defined above and $X^A$ represents

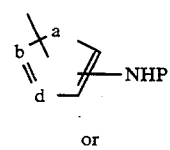

or

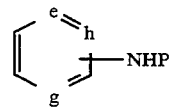

(wherein a, b, d, e, g and h are the same as defined above, and P is a protecting group of the amino group); $R^{2B}$ represents $-(CH_2)_m-X^B$ wherein m is the same as defined above and $X^B$ represents

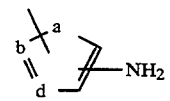

or

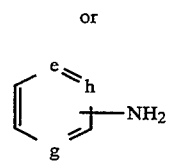

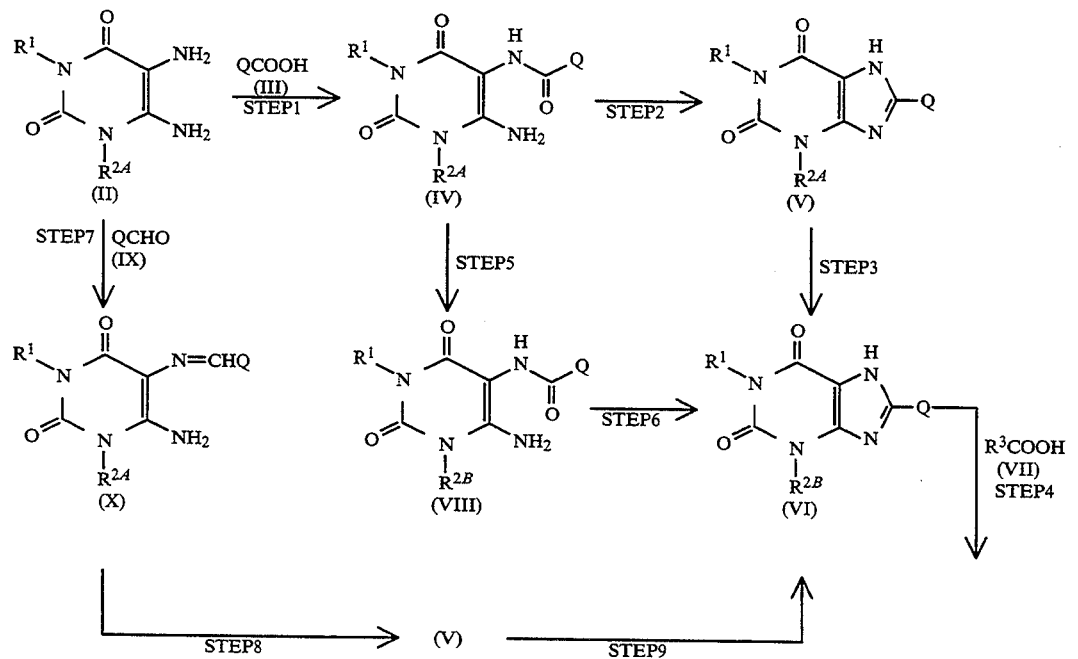

wherein $R^{2A}$ represents $-(CH_2)_m-X^A$

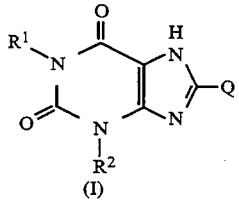

(wherein a, b, d, e, g and h are the same as defined above);
and $R^1$, $R^2$, $R^3$ and Q are the same as defined above.

As the protecting group of the amino group, there are tert-butoxycarbonyl, benzyloxycarbonyl, acetyl, formyl, and the like.

Step 1

Compound (IV) can be obtained by reaction of Compound (II) with Compound (III) or a reactive derivative thereof. Compound (II) can be prepared by a known method (Japanese Published Unexamined Patent Application No. 42383/84).

Examples of the reactive derivative of Compound (III) are acid halides such as acid chloride and acid bromide, active esters such as p-nitrophenyl ester and N-oxysuccinimide, acid anhydrides prepared by using carbodiimide such as 1-ethyl-3-(3-dimethylamino)-propylcarbodiimide, diisopropylcarbodiimide and dicyclohexylcarbodiimide, and mixed acid anhydrides with monoethyl carbonate and monoisobutyl carbonate.

The reaction is carried out using Compound (III) in an amount almost equivalent to Compound (II).

When Compound (III) is used, the reaction is carried out by heating to 50° C. to 200° C. in the absence of a solvent.

When the reactive derivative is used, the reaction can be carried out according to a common method in the field of peptide chemistry. For example, the reaction can be carried out in a solvent selected from halogenated hydrocarbons such as dichloromethane, chloroform and dichloroethane, ethers such as dioxane and tetrahydrofuran, dimethylformamide, dimethyl sulfoxide and water. The reaction is carried out at a temperature of −80° C. to 50° C. and is completed within 0.5 to 24 hours. If necessary, the reaction can be carried out in the presence of an additive such as 1-hydroxybenzotriazole or a base such as pyridine, triethylamine, 4-dimethylaminopyridine or N-methylmorpholine.

Step 2

Compound (V) can be obtained by ring-closure reaction of Compound (IV) in the presence of a base (Process A), by treatment with a dehydrating agent (Process B), or by heating (Process C).

(Process A)

Compound (V) can be obtained by reaction of Compound (IV) in a solvent in the presence of a base at a temperature of 4° C. to 180° C. for 10 minutes to 6 hours.

As the base, alkali metal hydroxides such as sodium hydroxide and potassium hydroxide, and the like may be used. As the solvent, water, lower alcohols such as methanol and ethanol, ethers such as dioxane and tetrahydrofuran, dimethylformamide, dimethyl sulfoxide, and the like may be used alone or in combination.

(Process B)

Compound (V) can be obtained by reaction of Compound (IV) in a solvent or in the absence of a solvent in the presence of a alehydrating agent at a temperature of 4° C. to 180° C. for 0.5 to 12 hours .

As the dehydrating agent, thionyl halides such as thionyl chloride, phosphorus oxyhalides such as phosphorus oxychloride, and the like may be used. As the solvent, halogenated hydrocarbons such as dichloromethane, chloroform and dichloroethane, dimethylformamide, dimethyl sulfoxide, and the like may be used.

(Process C)

Compound (V) can be obtained by heating Compound (IV) in a solvent at 50° C. to 200° C. for 1 to 20 hours.

As the solvent, dimethylformamide, dimethyl sulfoxide, Dowthermo A (Dow Chemical Co., Ltd.), and the like may be used.

Step 3

Compound (VI) can be obtained by deprotecting the protecting group P of Compound (V) according to a conventional method employed in the field of synthetic organic chemistry.

When the protecting group P is, for example, benzyloxycarbonyl group, catalytic hydrogenation is carried out with hydrogen gas in a solvent at an atmospheric pressure in the presence of a hydrogenation catalyst. The reaction is carried out at a temperature of 4° C. to 100° C. for 0.5 to 48 hours.

As the hydrogenation catalyst, platinum catalysts such as platinum oxide and activated carbon on platinum (Pt/C), palladium catalysts such as activated carbon on palladium (Pd/C) and palladium black, nickel catalysts such as Raney nickel, activated carbon on rhodium (Rh/C), and the like may be used. As the solvent, alcohols such as methanol and ethanol, esters such as ethyl acetate, ethers such as dioxane and tetrahydrofuran, N, N-dimethylformamide, acetic acid, and the like may be used.

Step 4

Compound (I) can be obtained by reaction of Compound (VI) with Compound (VII) or a reactive derivative thereof. The reaction may be carried out in the same way as in Step 1. In the reaction, Compound (VII) is used in an amount of 1 to 2.5 equivalents per 1 equivalent of Compound (VI).

Step 5

Compound (VIII) can be obtained from Compound (IV) according to the same procedure as that described in Step 3.

Step 6

Compound (VI) can be obtained from Compound (VIII) according to the same procedure as that described in Step 2.

Step 7

Compound (X) can be obtained by reaction of Compound (II) with Compound (IX) in a solvent at a temperature of −20° C. to 100° C. for 10 minutes to 5 hours.

In the reaction, Compound (IX) is used in an amount almost equivalent to Compound (II).

As the solvent, a mixture of acetic acid and a lower alcohol such as methanol or ethanol may be used.

Step 8

Compound (V) can be obtained by reaction of Compound (X) in a solvent in the presence of an oxidizing agent at 4° C. to 180° C. for 30 minutes to 10 hours.

As the oxidizing agent, oxygen, ferric chloride, ammonium cerium (IV) nitrate, diethyl azodicarboxylate, and the like may be used. As the solvent, lower alcohols such as methanol and ethanol, halogenated hydrocarbons such as dichloromethane and chloroform, aromatic hydrocarbons such as toluene, xylene and nitrobenzene, and the like may be used.

Step 9

Compound (VI) can be obtained from Compound (V) according to the same procedure as that described in Step 3.

The compounds formed in each of the steps described above can be isolated and purified by a conventional purification method usually employed in the field of synthetic organic chemistry such as filtration, extraction, washing, drying, concentration, recrystallization and various chromatographic processes.

The salts of Compounds (I) can be obtained by a conventional method usually employed in the field of synthetic organic chemistry. For example, when Compound (I) is obtained in a salt form, it may be purified directly; and when it is obtained in the free form, it is dissolved or suspended in a suitable solvent and an acid or a base is added to the resulting solution or suspension to form a salt.

Compounds (I) and pharmacologically acceptable salts thereof may form addition products with water or various solvents, and these addition products are also included in the scope of the present invention.

Some of Compounds (I) can exist in the form of optical isomers, and the present invention includes all possible stereoisomers and mixtures thereof.

Examples of Compounds (I) are shown in Table 1, in which the compounds of Nos. 1 to 8 are those obtained in Examples 1 to 8 described later, respectively.

TABLE 1

| Compound No. | R³ | Q |
|---|---|---|
| 1 | —CH₃ |  |
| 2 | —C₂H₅ | " |
| 3 | -n-C₃H₇ | " |
| 4 | -iso-C₃H₇ | " |
| 5 | | " |
| 6 | —CH₃ |  |

TABLE 1-continued

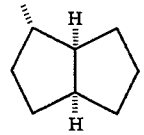

| Compound No. | R³ | Q |
|---|---|---|
| 7 | " | |
| 8 | " | 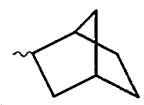 |

The pharmacological activity of Compound (I) is illustrated by the following experiment:

Experimental Data

The effect of Compound (I) on dementia was determined by scopolamine-induced amnesia models (Basic, Clinical, and Therapeutic Aspects of Alzheimer's and Parkinson's Diseases: Vol. 2; T. Nagatsu, et al. edt; pp449; Plenum Press New York; 1990).

Male Wistar rats (Charles River Laboratories) weighing 220 g to 280 g were used for the test, and each group consisted of 12 to 15 animals. The test was performed with a step-through type passive avoidance apparatus (the bright and dark box).

The bright and dark box was made up of a bright compartment (25×25×25 cm) lighted by 4W white fluorescent light and a dark compartment (25×25×25 cm). These two compartments were partitioned by a guillotine door (9×9 cm) and had a grid floor of stainless steel. In order to give a foot shock, the electric current (2 mA: 2 sec) may be passed through the grid floor of the dark compartment.

The compound to be tested was suspended in 0.3% aqueous solution of carboxymethyl cellulose (CMC) and the suspension was orally administered 60 minutes before the acquisition trial. Only 0.3% CMC was given to the control group.

Amnesia-inducing treatment was carried out by intraperitoneally administering 1 mg/kg of scopolamine 30 minutes before the following acquisition trial.

The training for acquisition of learning (acquisition trial) was carried out. The rat was introduced into the bright compartment, and after 5 to 10 seconds, the guillotine door was opened. The rat in the bright compartment rapidly moved into the dark compartment. As soon as the whole body of the rat entered the dark compartment, the guillotine door was closed and an electric current of 2 mA was passed through the grid floor for two seconds (foot shock). Immediately after the foot shock, the rat was taken out of the dark compartment.

The test trial for observing the retention and recall of the memory (recall trial) was carried out as follows. Twenty-four hours after the acquisition trial, the rat was placed in the bright compartment and the guillotine door was opened. The length of time before the rat entered the dark compartment (latency) was measured. The latency was measured up to 600 seconds and the latency longer than 600 seconds was recorded as 600 seconds.

In the experiment, the amnesia control group had undergone the amnesia-inducing treatment and the normal control group had not undergone the amnesia-inducing treatment.

The anti-dementia effect was evaluated by Mann Whitney U-test to determine whether there was a significant difference in latency between the test compound treated group and the amnesia control group. The results are shown in Table 2.

TABLE 2

| Test Compound | Dose (mg/Kg; oral) | Amnesia-inducing treatment | Number of animals | Recall trial mean reaction latency (sec.) | Comparison with amnesia control |
|---|---|---|---|---|---|
| Normal Control | 0 | — | 13 | 557.4 ± 21.6 | — |
| Amnesia Control | 0 | + | 17 | 36.0 ± 8.2 | * |
| Compound 1 | 0.02 | + | 17 | 137.3 ± 44.5 | No significant difference |
| | 0.08 | + | 18 | 174.8 ± 56.1 | $p < 0.05$ |
| | 0.31 | + | 18 | 130.4 ± 38.5 | $p < 0.01$ |
| | 1.25 | + | 17 | 170.3 ± 50.4 | $p < 0.05$ |
| | 5.0 | + | 18 | 187.2 ± 50.2 | $p < 0.001$ |
| | 20.0 | + | 17 | 116.2 ± 43.4 | No significant difference |

*Latency of amnesia control group is significantly shorter than latency of normal control ($p < 0.001$).

Acute Toxicity Test

Compounds 1 and 5 were orally administered to dd strain male mice (body weight: 20±1 g, 3 mice/group). The mortality was observed 7 days after the administration to determine the minimum lethal dose (MLD).

MLD of the compounds was >300 mg/kg. This is weak toxicity and therefore the compounds can be used safely in a wide dose range.

Compounds (I) and pharmacologically acceptable salts thereof can be used as they are or in various pharmaceutical composition forms.

The pharmaceutical compositions of the present invention can be prepared by uniformly mixing an effective amount of Compound (I) or a pharmacologically acceptable salt thereof as an active component and a pharmacologically acceptable carrier. The pharmaceutical compositions are preferably in a unit dose form suitable for oral administration or administration through injection.

For preparing a pharmaceutical composition for oral administration, any useful pharmacologically acceptable carrier can be used. For example, suspensions and syrups can be prepared using water, sugars such as sucrose, sorbitol and fructose, glycols such as polyethylene glycol and propylene glycol, oils such as sesame oil, olive oil and soybean oil, preservatives such as p-hydroxybenzoic acid esters, flavors such as strawberry flavor and peppermint, and the like. Powders, pills, capsules and tablets can be prepared using excipients such as lactose, glucose, sucrose and mannitol, disintegrating agents such as starch and sodium alginate, lubricants such as magnesium stearate and talc, binders such as polyvinyl alcohol, hydroxypropyl cellulose and gelatin, surfactants such as fatty acid esters, plasticizers such as glycerin, and the like. Tablets and capsules are most useful oral unit dose forms because of the readiness of administration.

Injectable preparations can be prepared using a carrier such as distilled water, a salt solution, a glucose solution or a mixture of a salt solution and a glucose solution. The preparations can be prepared in the form of solution, suspension or dispersion according to a conventional method by using a suitable auxiliary.

Compounds (I) and pharmacologically acceptable salts thereof can be administered orally in the said dosage forms or parenterally as injections. The effective dose and the administration schedule vary depending upon mode of administration, age, body weight and conditions of a patient, etc. However, generally, Compound (I) or a pharmacologically acceptable salt thereof is administered in a daily dose of 0.02 to 50 mg/kg in 3 to 4 parts.

Certain embodiments of the invention are illustrated in the following examples.

EXAMPLE 1

Compound i obtained in Reference Example 1 (1.0 g, 2.62 mmol) was dissolved in 180 ml of dichloromethane. Triethylamine (0.97 ml, 7.86 mmol) and 4-dimethylaminopyridine (64 mg, 0.52 mmol) were added to the solution. Anhydrous acetic acid (0.52 ml, 5.51 mmol) was added dropwise at room temperature, and the resulting mixture was stirred for two hours. Water (100 ml) was added to the reaction mixture and the organic layer was isolated. The aqueous layer was extracted three times with 50 ml of chloroform, and the extract was combined with the isolated organic layer. The combined mixture was dried over anhydrous sodium sulfate, and the solvent was evaporated under reduced pressure. The residue was purified by silica gel column chromatography (eluent: 3% -methanol/-chloroform), and the eluate was concentrated. The crude crystals thus obtained were recrystallized from ethanol to give 695 mg (yield: 63%) of 3-(4-acetylaminophenethyl)-8-cyclopentyl 1-propylxanthine (Compound 1) as white powder.

Melting point: >270° C.

Elemental analysis (%): $C_{23}H_{29}N_5O_3$

Calcd.: C 65.23, H 6.90, N 16.54

Found : C 65.26, H 7.05, N 16.54

IR (KBr) , $\nu_{max}(cm^{-1})$: 1699, 1661, 1647, 1533, 1504

NMR (270 MHz, DMSO-$d_6$), δ(ppm): 13.04 (1H, brs), 9.84 (1H, brs), 7.45(2H, d, J=8.4 Hz), 7.07(2H, d, J=8.4 Hz), 4.16(2H, t, J=7.4 Hz), 3.81(2H, t, J=6.9 Hz), 3.35-3.05(1H, m), 2.91(2H, t, J=7.4 Hz), 2.05-1.50(10H, m), 2.00(3H, s), 0.83(3H, t, J=7.4 Hz)
MS (m/e): 423 (M+)

EXAMPLE 2

Compound i obtained in Reference Example 1 (500 mg, 1.31 mmol) was dissolved in a mixture of 5 ml of pyridine and 50 ml of dichloromethane, and 15 mg (0.13 mmol) of 4-dimethylaminopyridine was added to the solution. Propionyl chloride (0.13 ml, 1.44 mmol) was added at 0° C. and the resulting mixture was stirred at room temperature for 20 minutes. The crystals formed were collected by filtration. Water was added to the filtrate, and the resulting solution was extracted three times with 30 ml of chloroform. The extract was dried over anhydrous sodium sulfate, and the solvent was evaporated under reduced pressure. The residue was purified by silica gel column chromatography (eluent: 5%-methanol/chloroform), and the eluate was concentrated. The crude crystals thus obtained were combined with the crystals collected above and recrystallized from dimethyl sulfoxide/water to give 380 mg (yield: 66%) of 3-(4-propionylaminophenethyl)-8-cyclopentyl-1-propylxanthine (Compound 2) as white powder.

Melting point: >270° C.
Elemental analysis (%): $C_{24}H_{31}N_5O_3$
Calcd.: C 65.88, H 7.14, N 16.00
Found : C 65.83, H 7.47, N 15.79
IR (KBr), $\nu_{max}(cm^{-1})$: 1698, 1650, 1523, 1500
NMR (270 MHz, DMSO-$d_6$), δ(ppm): 13.04 (1H, brs), 9.76(1H, brs), 7.47(2H, d, J=8.5 Hz), 7.07(2H, J=8.5 Hz), 4.17(2H, t, J=6.9 Hz), 3.81(2H, t, J=6.9 Hz), 3.35-3.05(1H, m), 2.90(2H, t, J=6.9 Hz), 2.29(2H, q, J=7.4 Hz), 2.05-1.50(10H, m), 1.06(3H, t, J=7.4 Hz), 0.83(3H, t, J=7.4 Hz)
MS (m/e): 437 (M+)

EXAMPLE 3

The procedure similar to that described in Example 2 was repeated except for the use of butyryl chloride (0.16 ml, 1.31 mmol) in place of propionyl chloride (0.13 ml, 1.44 mmol). The crude crystals obtained were recrystallized from ethanol to give 470 mg (yield: 80%) of 3-(4-butyrylaminophenethyl)-8-cyclopentyl-1-propylxanthine (Compound 3) as white powder.

Melting point: >270° C.
Elemental analysis (%): $C_{25}H_{33}N_5O_3$
Calcd.: C 66.49, H 7.36, N 15.50
Found : C 66.59, H 7.28, N 15.46
IR (KBr), $\nu_{max}(cm^{-1})$: 1690, 1643, 1494
NMR (270 MHz, DMSO-$d_6$), δ(ppm): 13.04(1H, brs), 9.77(1H, brs), 7.47(2H, d, J=8.4 Hz), 7.06(2H, d, J=8.4 Hz), 4.16(2H, t, J=6.9 Hz), 3.81(2H, t, J=6.9 Hz), 3.20-3.05(1H, m), 2.91(2H, t, J=6.9 Hz), 2.24(2H, t, J=6.9 Hz), 2.05-1.50(12H, m), 0.90(3H, t, J=6.9 Hz), 0.83(3H, t, J=7.4 Hz)
MS (m/e): 451 (M+)

EXAMPLE 4

The procedure similar to that described in Example 2 was repeated except for the use of isobutyryl chloride (0.16 ml, 1.31 retool) in place of propionyl chloride (0.13 ml, 1.44 mmol). The crude crystals obtained were recrystallized from ethanol to give 330 mg (yield: 56%) of 3-(4-isobutyrylaminophenethyl)-8-cyclopentyl-1-propylxanthine (Compound 4) as white powder.

Melting point: >270° C.
Elemental analysis (%): $C_{25}H_{33}N_5O_3$
Calcd.: C 66.49, H 7.36, N 15.50
Found : C 66.38, H 7.60, N 15.66
IR (KBr), $\nu_{max}(cm^{-1})$: 1701, 1655, 1516, 1498
NMR (270 MHz, DMSO-$d_6$), δ(ppm): 13.04(1H, brs), 9.73(1H, brs), 7.47(2H, d, J=8.4 Hz), 7.06(2H, d, J=8.4 Hz), 4.16(2H, t, J=7.4 Hz), 3.81(2H, t, J=6.9 Hz), 3.20-3.05(1H, m), 2.90(2H, t, J=7.4 Hz), 2.65-2.45(1H, m), 2.05-1.50(10H, m), 1.07(6H, d, J=6.9 Hz), 0.83(3H, t, J=7.4 Hz)
MS (m/e): 451 (M+)

EXAMPLE 5

Compound k obtained in Reference Example 2 (10.8 g, 35.3 mmol) was dissolved in a mixture of 100 ml of dioxane and 100 ml of water, and 3.86 ml (35.5 mmol) of cyclopentanecarboxylic acid was added to the solution. Then, 1-ethyl-3-(3-dimethylamino)propylcarbodiimide hydrochloride (11.2 g, 56.8 mmol) was added slowly at room temperature at pH 5-6 over a period of five minutes. The crystals formed were collected by filtration to give 7.13 g (yield: 41%) of 6-amino-1-[4-(cyclopentanecarbonylamino)phenethyl]-5-(cyclopentanecarbonyl) amino-3-propyluracil (Compound x) as white powder.

Compound x (7.03 g, 14.2 mmol) was then dissolved in a mixture of 90 ml of 2N aqueous solution of sodium hydroxide and 30 ml of dioxane and the solution was heated under reflux for 30 minutes. After cooling, the reaction mixture was neutralized with concentrated hydrochloric acid, and the crystals formed were collected by filtration. The obtained crystals were recrystallized from methanol and then from dioxane to give 2.64 g (yield: 39%) of 3-[4-(cyclopentanecarbonylamino)-phenethyl]-8-cyclopentyl-1-propylxanthine (Compound 5) as white crystals.

Melting point: >270° C.
Elemental analysis (%): $C_{27}H_{35}N_5O_3$
Calcd.: C 67.90, H 7.39, N 14.66
Found : C 67.75, H 7.41, N 14.72
IR (KBr), $\nu_{max}(cm^{-1})$: 1730, 1685, 1525
NMR (270 MHz, DMSO-$d_6$), δ(ppm): 13.04(1H, brs), 9.76(1H, brs), 7.47(2H, d, J=8.4 Hz), 7.05(2H, d, J=8.4 Hz), 4.16(2H, t, J=7.4 Hz), 3.81(2H, t, J=6.9 Hz), 3.15-3.00(1H, m), 2.90 (2H, t, J=7.4 Hz), 2.80-2.60(1H, m), 2.00-1.45(18H, m), 0.83(2H, t, J=7.4 Hz)

EXAMPLE 6

The procedure similar to that described in Example 1 was repeated except for the use of Compound n obtained in Reference Example 3 (470 mg, 1.09 mmol) in place of Compound i. 3-(4-Acetylaminophenethyl)-8-(3-noradamantyl)-1-propylxanthine (Compound 6) was obtained as pale brown powder (410 mg, yield: 79%).

Melting point: 251.5-252.4° C.
(Recrystallization from DMF/water)
Elemental analysis (%): $C_{27}H_{33}N_5O_3$
Calcd.: C 68.18, H 6.99, N 14.72
Found : C 68.33, H 6.91, N 15.11
IR (KBr), $\nu_{max}(cm^{-1})$: 1698, 1640, 1497
NMR (270 MHz, DMSO-$d_6$), δ(ppm): 12.9(1H, brs), 9.82(1H, brs), 7.44(2H, d, J=8.4 Hz), 7.07(2H, d, J=8.4 Hz), 4.18(2H, t, J=7.3 Hz), 3.83(2H, t, J=7.0 Hz), 2.89(2H, t, J=7.3 Hz), 2.57(1H, t, J=6.6 Hz), 2.35-2.25(2H, m), 2.20-2.10(2H, m), 2.00(3H, s), 2.00-1.85(4H, m), 1.70-1.50(6H, m), 0.84(3H, t, J=7.6 Hz)
MS (m/e): 475 (M+)

EXAMPLE 7

The procedure similar to that described in Example 1 was repeated except for the use of Compound o obtained in Reference Example 4 (940 rag, 2.23 mmol) in place of Compound i. 3-(4-Acetylaminophenethyl)-8-[(1R*, 2R*, 5R*)-bicyclo[3.3.0]octan-2-yl]-1-propylxanthine (Compound 7) was obtained as white powder (700 mg, yield: 68%).

Melting point: 219.5-220.5° C.
(Recrystallization from ethanol/water)
Elemental analysis (%): $C_{26}H_{33}N_5O_3$
Calcd.: C 67.36, H 7.17, N 15.10
Found : C 67.61, H 7.27, N 15.20
IR (KBr), $\nu_{max}$(cm$^{-1}$): 1702, 1638, 1498
NMR (270 MHz, CDCl$_3$), δ(ppm): 12.18(1H, brs), 7.40(2H, d, J=8.3 Hz), 7.23(2H, d, J=8.3 Hz), 7.15(1H, brs), 4.35(2H, t, J=7.4 Hz), 4.00(2H, t, J=7.2 Hz), 3.06(2H, t, J=7.4 Hz), 2.90-2.65(3H, m), 2.16(3H, s), 2.20-1.20(12H, m), 0.96(3H, t, J=7.3 Hz)
MS (m/e): 4 63 (M+)

EXAMPLE 8

The procedure similar to that described in Example 1 was repeated except for the use of Compound p obtained in Reference Example 5 (900 mg, 2.21 mmol) in place of Compound i. A 1:1 mixture of 3-(4-acetylaminophenethyl)-8[(1R*, 2R*, 5R*)-bicyclo[2.2.1]heptan-2-yl]-1-propylxanthine and (1R*, 2R*, 5S*) isomer (Compound 8) was obtained as pale yellow needles (680 mg, yield: 67%).

Melting point: 233.1-235.8° C.
(Recrystallization from ethanol/water)
Elemental analysis (%): $C_{25}H_{31}N_5O_3 \cdot \frac{1}{2}C_2H_5OH$
Calcd.: C 66.08, H 7.25, N 14.82
Found: C 65.95, H 7.37, N 14.92
IR (KBr), $\nu_{max}$(cm$^{-1}$): 1697, 1639, 1602, 1498
NMR (270 MHz, DMSO-d$_6$), δ(ppm): 9.81(1H, brs), 7.44(2H, d, J=8.2 Hz), 7.05(2×½H, d, J=8.2 Hz), 7.04(2×½H, d, J=8.2 Hz), 4.19(2×½H, t, J=7.4 Hz), 4.16(2×½H, t, J=7.4 Hz), 3.81(2H, t, J=7.0 Hz), 3.25-3.15(½H, m), 3.10-2.90(½H+2H, m), 2.45-2.25(2H, m), 2.10-1.10(10H, m), 2.00(3H, m), 0.83(3H, t, J=7.4 Hz)
MS (m/e): 449 (M+)

EXAMPLE 9 Tablets

Tablets each having the following composition are prepared in a conventional manner.

| | |
|---|---|
| Compound 1 | 10 mg |
| Lactose | 60 mg |
| Potato starch | 30 mg |
| Polyvinyl alcohol | 2 mg |
| Magnesium stearate | 1 mg |
| Tar pigment | trace |

REFERENCE EXAMPLE 1

4-Nitrophenethylamine (127 g, 0.767 tool) [J. Org. Chem., 43, 31 (1978)] was dissolved in 2.5 liters of toluene, and propyl isocyanate (72 ml, 0.764 mol) was slowly added dropwise at room temperature. The mixture was stirred for two hours, and the crystals formed were collected by filtration and dried under reduced pressure to give 171.5 g (yield: 89.8%) of 1-(4-nitrophenethyl)-3propylurea (Compound a).

IR (KBr), $\nu_{max}$(cm$^{-1}$): 3322, 2870, 1620, 1578, 1516
NMR (90 MHz, CDCl$_3$), δ(ppm): 8.10(2H, d, J=8.8 Hz), 7.35(2H, d, J=8.8 Hz), 4.95-4.50(2H, m), 3.70-3.30(2H, m), 3.25-2.75(6H, m), 1.70-1.30(2H, m), 0.90(3H, t, J=7.0 Hz)

Compound a (170 g, 0.677 mol) and cyanoacetic acid (63.3 g, 0.744 mol) were dissolved in 196 ml of anhydrous acetic acid, and the solution was heated at 75° C. for two hours. After the reaction mixture was concentrated under reduced pressure, 200 ml of water was added to the concentrate and the resulting solution was again concentrated under reduced pressure. The crude crystals thus obtained were recrystallized twice from ethyl acetate to give 42.9 g (yield: 19.9%) of 1-cyanoacetyl-3-(4-nitrophenethyl)-1-propylurea (Compound b).

Melting point: 99-101° C.
IR (KBr), $\nu_{max}$(cm$^{-1}$): 3386, 2876, 2260, 1693, 1678, 1518, 1503
NMR (90 MHz, CDCl$_3$), δ(ppm): 8.55(1H, brs ), 8.16(2H, d, J=8.7 Hz), 7.38(2H, d, J=8.7 Hz), 3.78(2H, s), 3.80-3.45(4H, m), 3.01(2H, t, J=7.0 Hz), 1.80-1.40(2H, m), 0.99(2H, t, J=7.0 Hz)
MS (m/e): 318 (M+)

A mixture of Compound b (57.5 g, 0.181 tool) and 2N aqueous solution of sodium hydroxide (680 ml) was stirred at 75° C. for 30 minutes. The reaction mixture was cooled, and the crystals formed were collected by filtration. The crystals were then washed with water and dried under reduced pressure to give 51.7 g (yield: 89.9%) of 6-amino-1-(4-nitrophenethyl)-3-propyluracil (Compound c).

IR (KBr), $\nu_{max}$(cm$^{-1}$): 1658, 1639, 1611, 1518, 1492
NMR (90 MHz, DMSO-d$_6$), δ(ppm): 8.10(2H, d, J=8.5 Hz), 7.47(2H, d, J=8.5 Hz), 6.82(2H, brs), 4.78(1H, s), 4.08(2H, t, J=7.2 Hz), 3.57(2H, t, J=7 Hz), 2.97(2H, t, J=7.2 Hz), 1.65-1.15(2H, m), 0.77 (2H, t, J=7 Hz)
MS (m/e): 318 (M+)

Compound c (20 g, 62.8 mmol) was dissolved in 100 ml of acetic acid, and 1 g of 10%-Pd/C was added to the solution, followed by stirring for eight hours in a stream of hydrogen. The reaction mixture was filtered and the filtrate was concentrated under reduced pressure. The concentrate was alkalized by addition of 1N aqueous solution of sodium hydroxide. The crystals formed were collected by filtration, washed with water and dried under reduced pressure to give 15.6 g (yield: 86.5%) of 6-amino-1(4-aminophenethyl)-3-propyluracil (Compound d).

IR (KBr), $\nu_{max}$(cm$^{-1}$): 1658, 1613, 1517
NMR (90 MHz, CDCl$_3$), δ(ppm): 7.00(2H, d, J=8.0 Hz), 6.67(2H, d, J=8.0 Hz), 4.82(1H, s), 4.20-3.70(6H, m), 2.90(2H, t, J=7.5 Hz), 1.80-1.50(4H, m), 0.95(3H, t, J=7.2 Hz)
MS (m/e): 288 (M+)

Compound d (7 g, 24.3 retool) was dissolved in 180 ml of tetrahydrofuran, and 120 ml of water and sodium hydrogen carbonate (4.13 g, 4 9.2 mmol) were added. The resulting solution was cooled to 5°-10° C., and 30% toluene solution of carbobenzoxy chloride (11.9 g, 20.8 mmol) was added dropwise at a pH maintained in the range of 8 to 9 with 2N aqueous solution of sodium hydroxide. After being stirred for 30 minutes, the reaction mixture was concentrated under reduced pressure. Water was added to the concentrate, and the insoluble material was separated by filtration. It was then dissolved in 500 ml of ethyl acetate by heating, and the solution was dried over anhydrous sodium sulfate and filtered. Then, the solvent was evaporated under reduced pressure to give 10.0 g (yield: 98.0%) of 6-amino-1-(4-benzyloxycarbonylaminophenethyl)-3-propyluracil (Compound e).

IR (KBr), $\nu_{max}$(cm$^{-1}$): 1706, 1660, 1606, 1527, 1511
NMR (90 MHz, DMSO-d$_6$), δ(ppm): 8.63(1H, brs), 7.65–7.20(7H, m), 7.11(2H, t, J=8.5 Hz), 5.15(2H, s), 4.67(1H, s), 3.99(2H, t, J=7.0 Hz), 3.62(2H, t, J=7.5 Hz), 2.73(2H, t, J=7.0 Hz), 1.55–1.25 (2H, m), 0.78(3H, t, J=7.5 Hz),
MS (m/e): 422 (M+)

Compound e (6.3 g, 14.0 retool) was dissolved in a mixture of 120 ml of ethanol and 40 ml of water, and 2.87 ml of concentrated hydrochloric acid was added at 30° C. Subsequently, sodium nitrite (1.82 g, 26.4 retool) was added thereto. The resulting solution was stirred for about 30 minutes, and the formed reddish violet crystals were collected by filtration. The crystals were then washed with water and dried under reduced pressure to give 8.66 g (yield: 82.3%) of 6-amino-1-(4-benzyloxycarbonylaminophenethyl)-5-nitroso-3-propyluracil (Compound f).

Melting point: 192.5–194.5° C.
IR (KBr), $\nu_{max}$(cm$^{-1}$): 1730, 1670, 1642, 1527, 1515
NMR (90 MHz, DMSO-d$_6$), δ(ppm): 9.62(1H, brs), 9.17(1H, brs), 7.45–7.20(7H, m), 7.08(2H, d, J=8.8 Hz), 5.12(2H, s), 4.06(2H, t, J=7.5 Hz), 3.79(2H, t, J=7.0 Hz), 2.75(2H, t, J=7.5 Hz), 1.70–1.25(2H, m), 0.84(3H, t, J=7.0 Hz)
MS (m/e): 451 (M+)

Compound f (6.3 g, 14.0 mmol) was suspended in 280 ml of 50% ethanol, and sodium hydrosulfite (9.7 g, 55.7 mmol) was added slowly to the suspension with stirring over a period of 30 minutes. The insoluble matters were filtered off and the filtrate was concentrated under reduced pressure. The formed crystals were collected by filtration, washed with water and dried under reduced pressure to give 5.23 g (yield: 85.7%) of 5,6-diamino-1-(4-benzyloxycarbonylaminophenethyl)-3-propyluracil (Compound g).
MS (m/e): 437 (M+)

Compound g (13.4 g, 30.6 mmol) was dissolved in 200 ml of dioxane, and 110 ml of water was added to the solution. Cyclopentanecarboxylic acid (3.86 g, 33.8 mmol) and 1-ethyl-3-(3-dimethylamino)propylcarbodiimide hydrochloride (6.41 g, 33.4 mmol) were then added to the solution, and the resulting mixture was stirred for 18 hours. The reaction mixture was concentrated under reduced pressure, and the concentrate was extracted with 400 ml of ethyl acetate. The extract was washed with 100 ml of water and dried over anhydrous sodium sulfate. The solvent was evaporated under reduced pressure to give 15.7 g (yield: 96.1%) of 6-amino-5-cyclopentanecarbonylamino-1-(4-benzyloxycarbonylaminophenethyl)-3-propyluracil (Compound h).
MS (m/e): 533 (M+)

Compound h (15.7 g, 29.4 retool) was dissolved in 70 ml of dioxane, and 170 ml of 2N aqueous solution of sodium hydroxide was added. The resulting solution was heated under reflux for one hour. The reaction mixture was concentrated under reduced pressure, and the concentrate was adjusted to pH 7. The crystals formed were collected by filtration, washed with water and dried under reduced pressure. The crude crystals thus obtained (9.6 g) were recrystallized from dioxane to give 6.80 g (yield: 60.6%) of 3-(4-aminophenethyl)-1-propyl-8cyclopentylxanthine (Compound i) as colorless powder.

Melting point: 248–250° C.
Elemental analysis (%): $C_{21}H_{27}N_5O_2$
Calcd.: C 66.11, H 7.13, N 18.36
Found : C 65.87, H 7.17, N 18.06
IR (KBr), $\nu_{max}$(cm$^{31\ 1}$): 1694, 1645, 1500
NMR (270 MHz, DMSO-d$_6$), δ(ppm): 13.05 (1H, brs), 6.84(2H, d, J=8.0 Hz), 6.47(2H, d, J=8.0 Hz), 4.87(2H, brs), 4.09(2H, t, J=7.4 Hz), 3.82(2H, t, J=6.9 Hz), 3.20–3.05(1H, m), 2.77(2H, t, J=7.4 Hz), 2.10–1.50(10H, m), 0.85(3H, t, J=7.4 Hz )
MS (m/e): 381 (M+)

REFERENCE EXAMPLE 2

Compound c obtained in Reference Example 1 (44.8 g, 141 mmol) was suspended in a mixture of 740 ml of ethanol and 250 ml of water, and the suspension was heated at 70° C. until a clear solution was obtained. After cooling, 17 ml of concentrated hydrochloric acid was added at a temperature of 40° C., and then 25 ml of an aqueous solution containing 10.7 g of sodium nitrite was added dropwise at a temperature of 35° C. over a period of five minutes. The reaction mixture was further cooled to 10° C., and the formed violet crystals were collected by filtration to give 42.1 g (yield: 72%) of 6-amino-1-(4-nitrophenethyl)-5-nitroso-3-propyluracil (Compound j).

Melting point: 204.5–205.2° C.
IR (KBr), $\nu_{max}$(cm$^{-1}$): 1684, 1547, 1463, 1442
NMR (90 MHz, DMSO-d$_6$), δ(ppm): 13.2(1H, brs), 9.30(1H, brs), 8.18(2H, d, J=8.4 Hz), 7.53(2H, d, J=8.4 Hz), 4.17(2H, t, J=8 Hz), 3.82(2H, t, J=8 Hz), 3.00(2H, t, J=8 Hz), 1.70–1.30(2H, m), 0.83(3H, t, J=8 Hz)

Compound j (10.3 g, 29.5 mmol) was suspended in a mixture of 100 ml of water and 50 ml of ethanol, and sodium hydrosulfite (30 g, 172 mmol) was added slowly at room temperature over a period of ten minutes. The reaction mixture was extracted three times with 300 ml of ethyl acetate . The extract was dried over anhydrous sodium sulfate, and the solvent was evaporated under reduced pressure to give 7.00 g (yield: 78%) of crude 1-(4-aminophenethyl) -5,6-diamino-3-propyluracil (Compound k).

Melting point: 186.8–187.7° C. (decomposition)
IR (KBr), $\nu_{max}$(cm$^{31\ 1}$): 3410, 3328, 1674, 1582, 1521, 1491
NMR (90 MHz, DMSO-d$_6$), δ(ppm): 6.92(2H, d, J=8.1 Hz), 6.48(2H, d, J=8.1 Hz), 6.10(2H, brs), 4.84(2H, brs), 3.96(2H, t, J=8 Hz), 3.72(2H, t, J=8 Hz), 2.91(2H, brs), 2.63(2H, t, J=8 Hz), 1.75–1.25(2H, m), 0.81(3H, t, J=8 Hz)

REFERENCE EXAMPLE 3

3-Noradamantanecarboxylic acid (2.79 g, 16.8 mmol) was dissolved in a mixture of tetrahydrofuran (50 ml) and methylene chloride (50 ml). 1-Hydroxybenzotriazole (2.57 g, 16.8 mmol) and 1-ethyl-3-(3-dimethylamino)propylcarbodiimide hydrochloride (3.22 g, 16.8 mmol) were added at 0° C., and the mixture was subjected to reaction at room temperature for 4 hours. To the resulting solution was added 4-dimethylaminopyridine (170 mg, 1.4 mmol), followed by addition of a solution of Compound g (6.12 g, 14.0 mmol) obtained in Reference Example 1 in a mixture of N,N-dimethylformamide (20 ml) and tetrahydrofuran (40 ml). After one hour, the reaction mixture was concentrated to about one-half of its original volume. After the addition of water (100 ml) to the concentrated mixture, the mixture was extracted three times with chloroform. The organic layers were combined, washed with a saturated aqueous solution of sodium chloride and dried over anhydrous sodium sulfate, and the solvent was evaporated under reduced pressure. The residue was purified by silica gel column chromatography (eluent: 2% methanol/98% chloroform) to give 6.95 g (yield: 85%) of 6-amino-5-(3noradamantane)carbonylamino-1-(4-benzyloxycarbonylaminophenethyl)-3-propyluracil (Compound L).

NMR (90 MHz, CDCl$_3$), δ(ppm): 7.99(1H, brs), 7.50–7.25(7H, m), 7.12(2H, d, J=7.8 Hz), 6.89(1H, brs), 5.20(2H, s), 4.25–3.65(6H, m), 3.05–2.75(3H, m), 2.45–1.45(14H, m), 0.90(3H, t, J=7.0 Hz)

Compound L (6.81 g, 11.6 mmol) was dissolved in ethanol (200 ml), and 10% Pd/C (600 rag) was added to the solution. The mixture was stirred for 15 hours in a stream of hydrogen. The catalyst was removed by filtration, and the filtrate was washed with ethanol and then concentrated. The residue was purified by silica gel column chromatography (eluent: 5% methanol/95% chloroform) and triturated with diethyl ether/hexane=3/1 (v/v) to give 3.63 g (yield: 69%) of 6-amino-1-(4-aminophenethyl)-5-(3-noradamantane)-carbonylamino-3-propyluracil (Compound m).

NMR (90 MHz, CDCl$_3$), δ(ppm): 7.32(1H, brs), 6.97(2H, d, J=8.5 Hz), 6.60(2H, d, J=8.5 Hz), 5.28(2H, brs), 4.20–3.75(4H, m), 3.27(2H, brs), 3.00–2.75(3H, m), 2.45–1.45(14H, m), 0.96(3H, t, J=7.0 Hz)

Compound m (3.50 g, 7.75 mmol) was dissolved in dioxane (80 ml), and 1N aqueous solution of sodium hydroxide (240 ml) was added to the solution. The mixture was heated under reflux for one hour. After cooling, the mixture was neutralized with concentrated hydrochloric acid, and the precipitated crystals were collected by filtration and dried under reduced pressure. Recrystallization from tetrahydrofuran gave 1.33 g (yield: 40%) of 3-(4-aminophenethyl)-8-(3-noradamantyl)-1-propylxanthine (Compound n).

Melting point: 283.7–285.2° C.
Elemental analysis (%): C$_{25}$H$_{31}$N$_5$O$_2$
Calcd.: C 69.25, H 7.20, N 16.15
Found : C 69.38, H 7.48, N 16.17
IR (KBr), ν$_{max}$(cm$^{-1}$): 1694, 1644, 1554, 1519, 1494
NMR (270 MHz, DMSO-d$_6$), δ(ppm): 13.0(1H, brs), 6.83(2H, d, J=8.4 Hz), 6.46(2H, d, J=8.4 Hz), 4.86(2H, brs), 4.10(2H, t, J=7.4 Hz), 3.83(2H, t, J=7.4 Hz), 2.78(2H, t, J=7.4 Hz), 2.61(1H, t, J=6.5 Hz), 2.35–2.25(2H, m), 2.20–2.10(2H, m), 2.00–1.85(4H, m), 1.70–1.50(6H, m), 0.86(3H, t, J=8.0 Hz)
MS (m/e): 433 (M+)

REFERENCE EXAMPLE 4

3-(4-Aminophenethyl)-8-[(1R*, 2R*, 5R*)-bicyclo[3.3.0]octan-2-yl]-1-propylxanthine (Compound o) 1.48 g, yield: 25%) was obtained according to the same procedure as that described in Reference Example 3, except that bicyclo[3.3.0]octane-2-carboxylic acid (1.70 g, 11.0 mmol) and Compound g obtained in Reference Example 1 (4.00 g, 9.14 mmol) were used, instead of 3-noradamantanecarboxylic acid (2.79 g, 16.8 mmol) and Compound g (6.12 g, 14.0 mmol).

Melting point: 237.1–238.1° C.
Elemental analysis (%): C$_{24}$H$_{31}$N$_5$O$_2$
Calcd.: C 68.38, H 7.41, N 16.61
Found : C 68.09, H 7.67, N 16.58
IR (KBr), ν$_{max}$(cm$^{-1}$): 1700, 1641, 1554, 1505
NMR (270 MHz, CDCl$_3$), δ(ppm): 12.27(1H, brs), 7.08(2H, d, J=8.4 Hz), 6.61(2H, d, J=8.4 Hz), 4.31(2H, t, J=7.9 Hz), 4.01(2H, t, J=7.8 Hz), 3.57(2H, brs), 2.97(2H, t, J=7.9 Hz), 2.90–2.65(3H, m), 2.20–1.25(12H, m), 0.97(3H, t, J=7.3 Hz)
MS (m/e): 421 (M+)

REFERENCE EXAMPLE 5

A 1:1 mixture of 3-(4-aminophenethyl)-8-[1R*, 2R*, 5R*)-bicyclo[2.2.1]heptan-2-yl]-1-propylxanthine and (1R*, 2R*, 5S*) isomer (Compound P) (1.47 g, yield: 40%) was obtained according to the same procedure as that described in Reference Example 3, except that bicyclo[2.2.1]heptane-2-carboxylic acid (1.54 g, 11.0 mmol) and Compound g obtained in Reference Example 1 (4.00 g, 9.14 mmol) were used instead of 3-noradamantanecarboxylic acid (2.79 g, 16.8 mmol) and Compound g (6.12 g, 14.0 mmol).

Melting point: 258.3–260.2° C.
IR (KBr), ν$_{max}$(cm$^{-1}$): 1704, 1649, 1520, 1496
NMR (270 MHz, DMSO-d$_6$), δ(ppm): 12.29(1H, brs), 6.83(2×½H, d, J=8.4 Hz), 6.82(2×½H, d, J=8.4 Hz), 6.45(2H, d, J=8.4 Hz), 4.86(2H, brs), 4.11(2×½H, t, J=7.4 Hz), 4.09(2×½H, t, J=7.4 Hz), 3.81(2H, t, J=7.0 Hz), 3.25–3.15(½H, m), 2.80–2.70(½H+2H, m), 2.60–2.25(2H, m), 2.10–1.10(10H, m), 0.85(3H, t, J=7.4 Hz)
MS (m/e): 407 (M+)

What is claimed is:
1. A xanthine derivative of the formula (I):

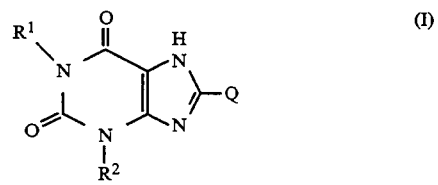

wherein R$^1$ represents lower alkyl which is optionally substituted with alicyclic alkyl having 3 to 8 carbon atoms, lower alkenyl, lower alkynyl, alicyclic alkyl which is optionally substituted with 1 to 3 substituents independently selected from the group consisting of alkyl having 1 to 6 carbon atoms, hydroxy, alkoxy having 1 to 6 carbon atoms, halogen, nitro and amino, phenyl which is optionally substituted with 1 to 3 substituents independently selected from the group consisting of alkyl having 1 to 6 carbon atoms, hydroxy, alkoxy having 1 to 6 carbon atoms, halogen, nitro and amino, or which is optionally substituted with 1 to 3 substituents independently selected from the group consisting of alkyl having 1 to 6 carbon atoms, hydroxy, alkoxy having 1 to 6 carbon atoms, halogen, nitro and amino;

R$^2$ represents —(CH$_2$)$_m$—X, wherein m is 2 or 3, and X is

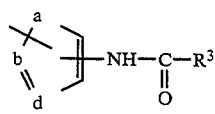

wherein a is NH, O or S, b and d are independently CH or N and $R^3$ is lower alkyl, alicyclic alkyl which is optionally substituted with 1 to 3 substituents independently selected from the group consisting of alkyl having 1 to 6 carbon atoms, hydroxy, alkoxy having 1 to 6 carbon atoms, halogen, nitro and amino, or phenyl which is optionally substituted with 1 to 3 substituents independently selected from the group consisting of alkyl having 1 to 6 carbon atoms, hydroxy, alkoxy having 1 to 6 carbon atoms, halogen, nitro and amino, or

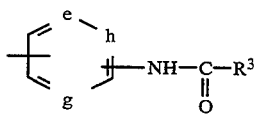

wherein e, g and h are independently CH or N, and $R^3$ is as defined above; Q represents alicyclic alkyl which is optionally substituted with 1 to 3 substituents independently selected form the group consisting of lower alkyl having 1 to 6 carbon atoms, hydroxy, alkoxy having 1 to 6 carbon atoms, halogen, nitro and amino,

wherein $R^4$ and $R^5$ are independently alicyclic alkyl which is optionally substituted with 1 to 3 substituents independently selected from the group consisting of lower alkyl having 1 to 6 carbon atoms, hydroxy, alkoxy having 1 to 6 carbon atoms, halogen, nitro and amino,

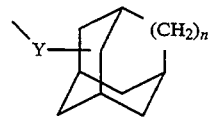

wherein Y is a single bond or alkylene; and n is 0 or 1,

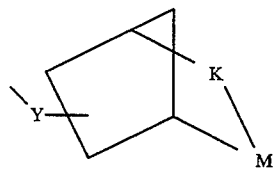

wherein K-M is —$CH_2$—$CH_2$— or —CH=CH—, and Y is as defined above, or

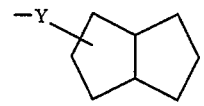

wherein Y is as defined above; or a pharmacologically acceptable salt thereof.

2. The xanthine compound according to claim 1, wherein $R^2$ represents

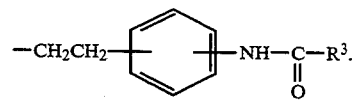

3. The xanthine compound according to claim 2, wherein Q represents

4. The compound according to claim 1, wherein said salt is selected from the group consisting of acid addition salts, metal salts, ammonium salts, organic amine addition salts and amino acid addition salts.

5. A pharmaceutical composition comprising a pharmacologically acceptable carrier and as an active ingredient, an effective amount of the derivative as defined by claim 1.

* * * * *

UNITED STATES PATENT AND TRADEMARK OFFICE
CERTIFICATE OF CORRECTION

PATENT NO. : 5,336,769

DATED : August 9, 1994

INVENTOR(S) : FUMIO SUZUKI, ET AL.

It is certified that error appears in the above-identified patent and that said Letters Patent is hereby corrected as shown below:

COLUMN 2

Line 44, "$R^e$" should read --$R^E$--.
Line 49, "No. 5068236" should read --No. 5,068,236-- and "Publishes" should read --Published--.
Line 62, "alkyl," should read --alkyl.--.
Line 65, "Publishes" should read --Published--.

Column 3

Line 26, "$-CH_2-CH_2-or$" should read -- $-CH_2-CH_2-$ or--.

COLUMN 4

Line 36, "$-CH_2-CH_2-or$" should read -- $-CH_2-CH_2-$ or--.
Line 37, "above" should read --above,--.

COLUMN 5

Line 2, "allcyclic" should read --alicyclic--.

COLUMN 7

Line 60, "alehydrating" should read --dehydrating--.

COLUMN 8

Line 8, "Step 3" should be centered.

UNITED STATES PATENT AND TRADEMARK OFFICE
CERTIFICATE OF CORRECTION

PATENT NO. : 5,336,769

DATED : August 9, 1994

INVENTOR(S) : FUMIO SUZUKI, ET AL.

It is certified that error appears in the above-identified patent and that said Letters Patent is hereby corrected as shown below:

COLUMN 13

Line 28, "$C_{24}H_{31}{}^{N}{}_5O_3$" should read --$C_{24}H_{31}N_5O_3$--.
Line 33, "(2H, J=8.5" should read --(2H, d, J=8.5--.
Line 64, "1.31 retool)" should read --1.31 mmol)--.

COLUMN 15

Line 7, "(940 rag," should read --(940 mg,--.
Line 24, "4 63 ($M^+$)" should read --463 ($M^+$)--.
Line 63, "0.767 tool)" should read --0.767 mol)--.

COLUMN 16

Line 28, "0.181 tool)" should read --0.181 mol)--.
Line 53, "6-amino-1" should read --6-amino-1- --.
Line 62, "24.3 retool)" should read --24.3 mmol)--.
Line 64, "4 9.2 mmol)" should read --49.2 mmol)--.

COLUMN 17

Line 18, "14.0 retool)" should read --14.0 mmol)--.
Line 21, "26.4 retool)" should read --26.4 mmol)--.
Line 45, "1(4-" should read --1-(4- --.
Line 63, "29.4 retool)" should read --29.4 mmol)--.

COLUMN 18

Line 5, "8cyclopentylxanthine" should read --8-cyclopentylxanthine--.
Line 11, "$v_{max}(cm^{31}{}^1)$:" should read --$v_{max}(cm^{-1})$:--.
Line 51, "$v_{max}(cm^{31}{}^1)$:" should read --$v_{max}(cm^{-1})$:--.

UNITED STATES PATENT AND TRADEMARK OFFICE
CERTIFICATE OF CORRECTION

PATENT NO. : 5,336,769
DATED : August 9, 1994
INVENTOR(S) : FUMIO SUZUKI, ET AL.

Page 3 of 3

It is certified that error appears in the above-identified patent and that said Letters Patent is hereby corrected as shown below:

COLUMN 19

Line 15, "(3noradamantane)" should read --(3-noradamantane)--.
Line 24, "(600 rag)" should read --(600 mg)--.

COLUMN 20

Line 62, "or" should read --or benzyl--.

COLUMN 21

Line 35, "form" should read --from--.

COLUMN 22

Line 19, "-CH$_2$-CH$_2$-or" should read -- -CH$_2$-CH$_2$- or--.

Signed and Sealed this

Twentieth Day of December, 1994

Attest:

BRUCE LEHMAN

Attesting Officer    Commissioner of Patents and Trademarks